United States Patent [19]

Weibull et al.

[11] 4,112,231

[45] Sep. 5, 1978

[54] PROCESS FOR THE CONDENSATION OF EPOXIDES WITH ORGANIC COMPOUNDS HAVING AN ACTIVE HYDROGEN

[75] Inventors: Bengt John Gustaf Weibull, Stenungsund; Leif Urban Folke Thorsell, Domsjoverken, both of Sweden

[73] Assignee: Berol Kemi AB, Stenungsund, Sweden

[21] Appl. No.: 719,646

[22] Filed: Sep. 1, 1976

[30] Foreign Application Priority Data

Sep. 5, 1975 [SE] Sweden .................................. 7509916

[51] Int. Cl.$^2$ ............................................. C07C 41/02
[52] U.S. Cl. ...................................... 544/174; 548/356; 260/615 B; 260/615 F; 260/615 R; 260/611 B; 260/611 R; 260/611 A; 260/584 B; 260/584 R; 260/563 R; 260/326.8; 260/326.5 R; 260/293.9; 544/374; 260/297 R; 260/326.16; 260/573; 544/401

[58] Field of Search ............ 260/615 B, 613 B, 611 B, 260/611 R, 611 A, 584 B, 563 R, 326.8, 326.5 R, 293.9, 268 R, 297 R, 326.16, 573, 584 R, 615 F, 615 R; 548/356; 544/174

[56] References Cited

U.S. PATENT DOCUMENTS

| 2,848,426 | 8/1958 | Newey ........................ 260/613 B X |
| 3,022,255 | 2/1962 | Morschel et al. ............ 260/615 B X |
| 3,219,631 | 11/1965 | Kullmar et al. ............. 260/615 B X |

*Primary Examiner*—Bernard Helfin

[57] ABSTRACT

A process is provided for the condensation of epoxides with organic compounds having an active hydrogen atom, such as alcohols, polyols, and amines, in the presence of a neutral inorganic salt selected from the group consisting of sodium fluoborate, magnesium perchlorate, calcium perchlorate, manganese perchlorate, nickel perchlorate and zinc perchlorate.

13 Claims, No Drawings

PROCESS FOR THE CONDENSATION OF EPOXIDES WITH ORGANIC COMPOUNDS HAVING AN ACTIVE HYDROGEN

Epoxides condense with organic compounds having an active hydrogen atom in the presence of an alkaline or acidic catalyst. Among the alkaline catalysts that have been used are the alkali metal hydroxides and alcoholates, such as sodium or potassium hydroxide and sodium or potassium alcoholates. Compounds having an active hydrogen atom that readily react include monohydric alcohols and polyols; amines, phenols and carboxylic acids. Polyoxyalkylene alcohols are obtained from alkylene glycols and higher polyols, oxyalkylated phenols from a phenol, and oxyalkylated esters from carboxylic acids. Polyoxyalkylene alcohols used in the preparation of polyurethane foams are obtained by the condensation of ethylene oxide and/or propylene oxide with glycols and polyols such as glycerol, pentaerythritol and polyethylene glycols.

The reaction proceeds in the following manner:

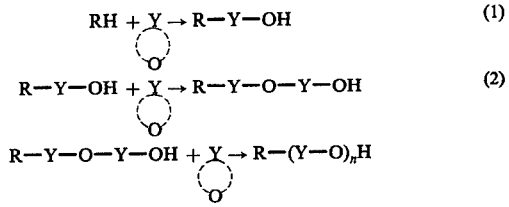

In the above formulae, R represents the residue of an alcohol or polyol, amine, carboxylic acid, or phenol, and Y a bivalent radical containing the epoxide group

The number $n$ of units —Y—O— of the epoxide added to the organic compound depend upon the organic compound and the epoxide and the number of moles of epoxide present, as well as the catalyst. A mixture of condensation product species is obtained, containing different molecular proportions of epoxide according to the organic compound, epoxide and the catalyst. Thus, reaction products having a wide range of molecular weights and of molecular distribution of the epoxide units can be obtained.

The uniformity of distribution of the various molecular species present is quite difficult to control. It is normally desirable to restrict the molecular distribution of the mixture to adjacent analogues of the desired product, insofar as possible, but this is quite difficult to do. Acidic catalysts tend to give a narrower molecular distribution then alkaline catalysts, but also contribute to the formation of undesired by-products, with the result that alkaline catalysts are normally employed, as the more efficient of the two types, even though the molecular distribution is more diffuse.

Certain inorganic salts, particularly the nitrates, sulphates, and halides, react with epoxides, so that the reaction medium containing them becomes alkaline as the reaction proceeds. Such salts accordingly behave as alkaline catalysts in influencing the course of the reaction, and offer no advantage over for example the alkali metal hydroxides. Other salts such as aluminum chloride and iron chloride form acids in the reaction mixture, as a result of hydrolysis or alcoholysis, and consequently behave as acidic catalysts, and offer no advantage over the acidic catalysts.

In accordance with the invention it is now been determined that certain inorganic fluoborates and perchlorates, which are neutral salts, catalyze the reaction of epoxides with organic compounds having an active hydrogen, and selected from the group consisting of monohydric alcohols, polyols and amines, and remain neutral, i.e., develop an appreciable acidity or alkalinity, in the course of the reaction. These catalysts not only accelerate the reaction but also favor a narrower molecular distribution, i.e., a more limited range of molecular species, and a larger proportion of the desired species, in the reaction product. The molecular distribution of the reaction product mixture tends to be concentrated to the adjacent and next adjacent homologues. This is particularly true of the reaction between ethylene oxide and primary and secondary alcohols and polyols.

Accordingly, in the process of the invention an organic compound having an active hydrogen and selected from the group consisting of monohydric alcohols, polyols and amines is reacted with an epoxide at a temperature at which the reaction proceeds in the presence of an inorganic salt catalyst selected from the group consisting of sodium fluoborate and magnesium, calcium, manganese, nickel and zinc perchlorates. The preferred catalyst is zinc perchlorate.

A catalytic effect is noted at a catalyst concentration of 0.001% by weight of the organic compound. There is no upper limit on the amount of catalyst, but in general at amounts in excess of 10% an enhanced catalytic effect proportionate to the amount used is no longer observed. Concentrations within the range from about 0.01 to about 1% are usually preferred. However, organic compounds having more than seven carbon atoms may give a better reaction at larger amounts of catalyst within the range from about 0.5 to about 5% by weight of the organic compound.

The reaction proceeds at an elevated temperature, and the reaction rate increases as the reaction temperature increases. Consequently, a given reaction rate at low reaction temperatures is obtained at high reaction temperatures using a smaller amount of catalyst.

In general, the reaction proceeds at reaction temperatures within the range from about 80° to about 200° C, and preferably within the range from about 100° to about 150° C. The reaction temperature is in all cases below the decomposition temperature of the reaction mixture, including the starting materials and the reaction products.

If desired, the reaction mixture can include an inert organic solvent. However, an excess of the organic compound having an active hydrogen can also be used, and will serve as the solvent. The amount of solvent is in no way critical, but it must of course be borne in mind that an excessively dilute reaction mixture reacts more slowly, and less efficiently.

The reaction is normally carried out in a pressure vessel, when low boiling epoxides are used, such as ethylene oxide or propylene oxide. Pressure may be unnecessary with less volatile epoxides.

The reaction is applicable to any organic compound having an active hydrogen atom. Among the organic compounds which can be employed the most important are the alcohols (including polyols), carboxylic acids, amines and phenols having from about one to about thirty carbon atoms.

The primary and secondary monohydric aliphatic alcohols are of particular importance. These can be straight or branched chain. Among the primary and straight chain monohydric alcohols are methanol, ethanol, butanol, pentanol, hexanol, heptanol, octanol, nonanol, decanol, dodecanol, tridecanol, tetradecanol, pentadecanol, hexadecanol, octadecanol, arachidyl, behenyl, lignoceryl and triacontanyl alcohols. Other suitable aliphatic alcohols include isopropyl alcohol, 2-ethylhexanol, sec.-butanol, iso-butanol, 2-pentanol, 3-pentanol, isooctanol, isononanol, sec.-octanol, and isodecanol.

The process of the invention is also applicable to cycloaliphatic monohydric alcohols, including cyclohexanol, cyclopentanol, cycloheptanol, cyclopropanol, and cyclooctanol, as well as phenyl-substituted monohydric alcohols such as benzyl alcohol, phenethyl alcohol, cinnamyl alcohol, and phenpropyl alcohol.

Also useful are the halogen-substituted alcohols such as chloroethanol, chloropropanol, chlorobutanol, bromoethanol, bromopropanol, bromobutanol, difluoroethanol, fluorochloropropanol, trifluoropropanol, and trichloropropanol.

Also of importance are the polyols having from two to thirty carbon atoms and from two to six hydroxyl groups, including the glycols, such as ethylene glycol, propylene glycol, butylene glycol, pentylene glycol, hexylene glycol, heptylene glycol, neopentylene glycol, decylene glycol, diethylene glycol, triethylene glycol, propylene glycol, dipropylene glycol, tripropylene glycol, glycerol, pentaerythritol, dulcitol, sorbitol, mannitol, erythritol, trimethylolethane, and trimethylolpropane.

Both primary and secondary monoamines undergo the reaction, including the primary and secondary aliphatic and cycloaliphatic amines, such as, for example, methylamine, ethylamine, propylamine, butylamine, pentylamine, hexylamine, heptylamine, octylamine, nonylamine, decylamine, dodecylamine, tetradecylamine, octadecylamine, dimethylamine, dipropylamine, methylethylamine, diethylamine, dibutylamine, butylethylamine, diamylamine, dihexylamine, diheptylamine, dioctylamine, methyloctylamine, dinonylamine, didecylamine, didodecylamine, and dioctadecylamine; cyclohexylamine, dicyclohexylamine, cyclopentylamine, dicyclopentylamine, cycloheptylamine, dicyclopheptylamine, methylcyclopentylamine, cyclooctylamine, and ethylcyclooctylamine.

In addition to the monoamines, diamines can be used, such as the alkylene diamines, for example ethylene diamine, diethylene triamine, triethylene tetraamine, propylene diamine, dipropylene triamine, butylene diamine, and dibutylene triamine. Heterocyclic amines such as pyrrole, pyrrolidine, piperazine, pyridine, morpholine, piperidine, pyrazole, pyrazoline, and indole can be used.

Also useful are the aromatic amines, such as aniline and alkyl- and halogen-substituted aromatic amines as well as N-substituted aromatic amines, such as N-methyl aniline, N-ethyl aniline; p-anisidine, and p-phenetidine.

The organic compound may contain both amino and hydroxyl groups, such as monoethanolamine, diethanolamine and triethanolamine, monopropanolamine, dipropanolamine, and tripropanolamine.

The catalyst of the invention will catalyze the reaction of any epoxide having from two to about thirty carbon atoms with any organic compound having a reactive hydrogen. Exemplary alkylene epoxides include ethylene oxide; propylene oxide-1,2; butylene oxide-1,2 and -2,3; pentylene oxide-1,2; hexylene oxide-1,2; octylene oxide-1,2; and decylene oxide-1,2, and the epoxidized fatty alcohols derived from fatty oils such as epoxidized soybean fatty alcohols and epoxidized linseed oil fatty alcohols. Exemplary cycloalkylene epoxides include cyclohexene oxide; cyclopentene oxide; cycloheptene oxide; aromatic epoxides include styrene oxide; α-methyl styrene oxide; and hydroxy- and halogen-substituted epoxides such as glycidol, epichlorohydrin and epibromhydrin.

The following Examples in the opinion of the inventors represent preferred embodiments of the invention:

EXAMPLES 1 AND 2

In an autoclave of acid-proof steel, fitted with a stirrer and heating or cooling bath, there were charged 337 grams (7.3 moles) of ethanol and 4.9 grams of catalyst. Three catalysts were used, sodium hydroxide (Control B), magnesium perchlorate (Example 1), and zinc perchlorate (Example 2). In addition, a control run (Control A) was made without a catalyst.

In each run, the autoclave was closed following addition of the ethanol and catalyst, and the air was expelled by repeated evacuations and flushings with nitrogen gas. The temperature was then brought to 120° C, and liquid ethylene oxide introduced, at such a rate that the pressure did not exceed 700 kPa (7kp/cm$^2$). The addition of ethylene oxide was discontinued when 322 grams (7.3 moles) had been introduced. The temperature was then held at 120° C until the pressure had decreased to a constant value, indicating that all of the ethylene oxide had reacted. The autoclave was then cooled, opened, and its contents analyzed.

Upon dilution with distilled water, the reaction product gave a practically neutral reaction (ph 5.7). The composition was determined by gas chromatography, using a Perkin-Elmer Gas Chromatograph, Model 900, with 1 m column of ⅜ inch diameter aluminum tube filled with Chromosorb 103, and at a programmed rate of temperature increase of 12° C/min., from 50° to 270° C. The analytical results are reported in Table I below, as apparent percent of the total, assuming all the reaction product was the oxyethylene adduct found, since all reaction products were not determined.

TABLE I

| Example No. | Catalyst | Rate[1] | Composition (Apparent Percent)[2] | | | | | |
|---|---|---|---|---|---|---|---|---|
| | | | None | One | Two | Three | Four | Five |
| Control A | — | 0.4 | — | — | — | — | — | — |
| Control B | NaOH | 2.5 | 29.3 | 23.2 | 19.7 | 13.4 | 8.0 | 4.0 |
| 1 | Mg(ClO$_4$)$_2$ | 2.0 | 18.9 | 39.5 | 26.4 | 11.0 | 3.4 | 0.8 |
| 2 | Zn(ClO$_4$)$_2$ | 13.3 | 18.4 | 45.1 | 25.3 | 8.8 | 2.0 | 0.4 |

TABLE I-continued

| Example No. | Catalyst | Rate[1] | Composition (Apparent Percent)[2] | | | | | |
|---|---|---|---|---|---|---|---|---|
| | | | None | One | Two | Three | Four | Five |
| | 6 H$_2$O | | | | | | | |

[1]Average amount of ethylene oxide reacted per minute.
[2]Number of moles of ethylene oxide reacted per mole of ethanol.

The catalytic effect using the catalyst in accordance with the invention is apparent from the above results as compared to no catalyst (Control A). The reaction rate is equal to that obtained using sodium hydroxide (Control A), and the molecular distribution of the reaction products is more favorable, since by far a major proportion of the reaction product is composed of the monoethoxylated product, a ratio of 1:1, which corresponds to the ratio of the number of moles of ethylene oxide added, 7.3, to 7.3 moles of ethanol. In the case of sodium hydroxide, only 23.2% of the product was the monoethoxylated product, whereas in the case of magnesium perchlorate (Example 1) 39.5% of the product was this material, and in the case of zinc perchlorate (Example 2) 45.1% was this material, roughly twice that in the case where the sodium hydroxide catalyst was used. Moreover, a smaller amount of the starting material, ethanol, remained unreacted, and a smaller amount of higher condensation products was formed.

EXAMPLES 3 TO 8

In an autoclave of acid-proof steel, fitted with a stirrer and heating or cooling bath, there were charged 307 grams (5 moles) of isopropyl alcohol and 9 grams of the catalyst noted in Table II below. The catalysts used included sodium hydroxide (Control), sodium fluoborate (Example 3), magnesium perchlorate (Example 4), calcium perchlorate (Example 5), manganese perchlorate (Example 6), nickel perchlorate (Example 7), and zinc perchlorate (Example 8).

In each run, the autoclave was closed following addition of the isopropyl alcohol and catalyst, and the air was expelled by repeated evacuations and flushings with nitrogen gas. The temperature was then brought to 120° C, and liquid ethylene oxide introduced, at such a rate that the pressure did not exceed 700 kPa (7 kp/cm$^2$). The addition of ethylene oxide was discontinued when 220 grams (5 moles) had been introduced. The temperature was then held at 120° C until the pressure had decreased to a constant value, indicating that all of the ethylene oxide had reacted. The autoclave was then cooled, opened, and its contents analyzed.

Upon dilution with distilled water the reaction product gave a practically neutral reaction (pH 5.7). The composition was determined by gas chromatography, using a Perkin-Elmer Gas Chromatograph Model 900 with 1 m column of ⅛ inch aluminum tube, filled with Chromosorb 103, and at a programmed rate increase of temperature of 12° C/min., from 50° to 270° C. The analytical results are reported in Table II below as apparent percent, since all reaction products were not determined.

TABLE II

| Example No. | Catalyst | Rate[1] | Composition (Apparent Percent) | | | | | |
|---|---|---|---|---|---|---|---|---|
| | | | None | One | Two | Three | Four | Five |
| Control | NaOH(0.1%) | 4.0 | 61.1 | 11.0 | 8.3 | 6.0 | 4.9 | 3.5 |
| 3 | NaBF$_4$ | 0.3 | 28.4 | 35.0 | 24.6 | 9.9 | 2.1 | — |
| 4 | Mg(ClO$_4$)$_2$ | 2.8 | 26.5 | 39.3 | 23.1 | 8.3 | 2.2 | 0.6 |
| 5 | Ca(ClO$_4$)$_2$ | 0.3 | 34.6 | 41.7 | 18.3 | 4.7 | 0.8 | — |
| 6 | Mn(ClO$_4$)$_2$-8 H$_2$O | 1.8 | 24.9 | 36.6 | 24.4 | 9.9 | — | — |
| 7 | Ni(ClO$_4$)$_2$-6 H$_2$O | 1.5 | 30.2 | 33.6 | 22.0 | 9.8 | 3.3 | 1.1 |
| 8 | Zn(ClO$_4$)$_2$-6 H$_2$O | 5.6 | 28.2 | 34.8 | 22.8 | 10.0 | 3.4 | 0.8 |

[1]Average amount of ethylene oxide reacted per minute.
[2]Number of moles of ethylene oxide reacted per mole of isopropyl alcohol.

It is apparent from the above results that the sodium hydroxide is far inferior. The amount of isopropyl alcohol remaining unreacted was 61.1%, approximately twice that in any of the runs using a catalyst in accordance with the invention. Similarly, the composition of the reaction product was much less favorable. In the case of the catalysts of the invention, from 33 to 41% of the reaction product was the monoethoxylated product, having a 1:1 molar ratio, whereas in the case of the sodium hydroxide this was only 11%, even though this was the most of any species present. The higher adducts extended all the way to the 5:1 product. Thus, the catalysts in accordance with the invention gave a superior molecular distribution. Moreover, zinc and magnesium perchlorates gave an excellent reaction rate.

EXAMPLES 9 TO 14

In a series of test runs, the reaction rate in the reaction between ethanol and ethylene oxide was determined, in the presence of varying amounts of zinc perchlorate, at different temperatures.

The reactions were carried out in an 85 ml autoclave of acid proof steel. A manometer was connected to the autoclave via a pressure-sensing means including a membrane of a volume of about 50 mls.

In each run, 72 grams of ethanol and 8 grams of ethylene oxide were charged, as well as the amount of catalyst indicated in Table III below. After the reactants were charged to the vessel, the vessel was sealed, and the vessel and pressure sensing means were immersed in a heating bath and brought to the temperature indicated in the Table. The pressure was recorded as a function of time until the pressure had dropped to a constant level.

The concentration of ethylene oxide at any time in the course of the action can be considered approximately proportional to the difference between the actual pressure and the pressure after it has ceased. The reaction was a first order reaction, so that the following equation applies with good accuracy:

$$ln(p_o - p_s)/(p - p_s) = k \cdot t$$

wherein $p_o$ is the pressure at the beginning of the reaction, $p_s$ is the pressure at the end of the reaction, and $p$ is the pressure at the time $t$. The velocity constant, $k$, can be obtained as the slope of the straight line obtained when plotting $ln(p - p_s)$ against $t$. However, it is more convenient to use the half-life, $t_{\frac{1}{2}}$, of the reaction, for which the following equation applies:

$$t_{\frac{1}{2}} = ln2/k$$

Table III summarizes the results obtained. For comparison purposes, a run (Control B) was made using 0.04% potassium hydroxide as catalyst. A run (Control A) was also carried out using no catalyst, but in this case the reaction had to be carried out at a higher temperature in order for the reaction to proceed at a measurable rate. From the results obtained, the half-times at lower temperature were calculated by extrapolation by means of Arrhenius' equation; the values are given in Table III.

TABLE III

| Example No. | Catalyst and % | | Half-time, minutes, at °C | | | |
|---|---|---|---|---|---|---|
| | | | 100° | 120° | 130° | 150° |
| Control A | none | — | — | — | 104 | — | 65 |
| Control B | KOH | 0.04 | 29 | 11 | 7 | 4 |
| 9 | | 0.001 | — | — | — | 47 |
| 10 | | 0.005 | — | — | — | 17 |
| 11 | Zn(ClO$_4$)$_2$ | 0.01 | — | — | 7 | 8 |
| 12 | 6H$_2$O | 0.02 | 37 | 11 | 4 | 4 |
| 13 | | 0.03 | — | 6 | — | — |
| 14 | | 0.04 | — | 7 | — | — |

The results in Table III show that the catalytic effect of zinc perchlorate is observed at a concentration as low as 0.001%. The reaction rate increases proportionate to the amount of catalyst. At a concentration of 0.02%, zinc perchlorate gives approximately the same catalytic effect as 0.04% potassium hydroxide. The catalytic activity also increases with temperature.

Zinc perchlorate gave a relatively smaller amount of the higher oxyethylated products than potassium hydroxide. Using potassium hydroxide, the content of monoethylether of diethylene glycol in the reaction product was about 3.7%, whereas when using zinc perchlorate, it was about 1.9%, about half as much.

EXAMPLE 15

To perchloric acid (11.5 grams of 70% perchloric acid, dissolved in 200 mls of ethanol), was added, with stirring, at 40° C, 4 grams of zinc oxide. When the solution had become neutral, the excess of zinc oxide was filtered off, and the filtrate was used in the reaction of ethanol with ethylene oxide as zinc perchlorate.

The catalyst prepared in accordance with this procedure was used in the procedure described in Examples 9 to 14, at a concentration of 0.014% by weight and a temperature of 150° C, and gave a half time of 3 minutes. It was as efficient as zinc perchlorate used as such.

EXAMPLE 16

In an autoclave of acid-proof steel fitted with a stirrer and heating or cooling bath, there were charged 186 grams (1 mole) of lauryl alcohol and 2.8 g (1.5% by weight) of zinc perchloride. In addition, a control run was made with potassium hydroxide as the catalyst.

In each run, the autoclave was closed following addition of the lauryl alcohol and catalyst, and the air was expelled by repeated evacuations and flushings with nitrogen gas. The temperature was then brought to 130° C, and liquid ethylene oxide introduced at such a rate that the pressure did not exceed 700 kPa (7 kp/cm$^2$). The addition of ethylene oxide was discontinued when 132 grams (3 moles) had been introduced. The temperature was then held at 130° C until the pressure became constant, indicating that all of the ethylene oxide had reacted. After about 5 hours of reaction, the autoclave was then cooled, opened, and its contents analyzed.

Upon dilution with distilled water, the reaction product gave a practically neutral reaction (pH 5.7). The composition was determined by gas chromatography using a Perkin-Elmer Gas Chromatograph Model 900 with 1 m column of ⅛ inch aluminum tube filled with Chromosorb 103, and at a programmed rate of increase of temperature of 12° C/min., from 50° to 270° C. All of the ethylene oxide had reacted and the product contained 2.3% unreacted lauryl alcohol.

In the control run, carried out exactly the same way but using 0.5% potassium hydroxide in place of the 1.5% zinc perchlorate, the amount of unreacted lauryl alcohol was 12.4%.

Thus, the ethylene oxide reacts more completely with the lauryl alcohol in the presence of zinc perchlorate than in the presence of potassium hydroxide.

EXAMPLE 17

In an autoclave of acid-proof steel, fitted with a stirrer and heating or cooling bath, there were charged 130 grams (1 mole) of 2-octanol and 2 g. (1.5%) zinc perchlorate.

The autoclave was closed following addition of the 1,2-octanol and catalyst, and the air was expelled by repeated evacuations and flushings with nitrogen gas. The temperature was then brought to 130° C, and liquid ethylene oxide introduced at such a rate that the pressure did not exceed 700 kPa (7 kp/cm$^2$). The addition of ethylene oxide was discontinued when 44 grams (1 mole) had been introduced. The temperature was held at 130° C for a total reaction time of 3.5 hours, when the pressure became constant, indicating that all of the ethylene oxide had reacted. The autoclave was then cooled, opened and its contents analyzed.

Upon dilution with distilled water the reaction product gave a practically neutral reaction (pH 5.7). The composition was determined by gas chromatography using a Perkin-Elmer Gas Chromatograph Model 900 with 1 m column of ⅛ inch aluminum tube filled with Chromosorb 103, and at a programmed rate of increase of temperature of 12° C/min., from 50° to 270° C.

The product was found to be composed of 36% unreacted 2-octanol, 36% of the 2-octylether of ethylene glycol, and 27% of 2-octylether of diethylene glycol.

Thus, the catalyst of the invention gives a straightforward addition reaction with secondary alcohols as well as primary alcohols. This is unusual, since secondary alcohols are known to react more slowly with ethylene oxide than their adducts, as a result of which recovery of initial adducts in the reaction product is poor.

EXAMPLES 18 AND 19

In an autoclave of acid-proof steel fitted with a stirrer and heating or cooling bath there were charged 58 grams (1 mole) of allyl alcohol and 0.87 g (1.5%) zinc perchlorate.

Another run was made with chloroethanol (40.1 g, one mole) and 0.6 g (1.5%) zinc perchlorate as catalyst.

In each run, the autoclave was closed following addition of the allyl alcohol or chloroethanol and catalyst, and the air was expelled by repeated evacuations and flushings with nitrogen gas. The temperature was then brought to 120° C and liquid ethylene oxide introduced at such a rate that the pressure did not exceed 700 kPa (7 kp/cm²). The addition of ethylene oxide was discontinued when 44 grams (1 mole) had been introduced. The temperature was then held at 120° C until the pressure became constant, indicating that all of the ethylene oxide had reacted. The autoclave was then cooled, opened, and its contents analyzed.

Upon dilution with distilled water, the reaction product gave a practically neutral reaction (pH 5.7). The composition was determined by gas chromatography using a Perkin-Elmer Gas Chromatograph Model 900 with 1 m column of ⅛ inch aluminum tube filled with Chromosorb 103, and at a programmed rate of increase of temperature of 12° C/min., from 50° to 270° C. The analytical results are reported in Table IV below as apparent percent, since all reaction products were not determined.

TABLE IV

| Ex. No. | Alcohol | Reaction time hrs. | Compositon (Apparent Percent)[1] | | | | | |
|---|---|---|---|---|---|---|---|---|
| | | | None | One | Two | Three | Four | Five |
| 18 | Allyl alcohol | 6 | 32 | 38 | 20 | 8 | — | — |
| 19 | Chloroethanol | 3 | 31 | 23 | 21 | 16 | 7 | 2 |

[1]Number of moles of ethylene oxide reacted per mole of isopropyl alcohol.

It is not possible to use an alkali metal hydroxide as a catalyst in the reaction with chloroethanol, since the chloroethanol reacts with alkali metal hydroxides.

It is apparent from the above results that good reactions were obtained, to produce primarily the monoethoxylated (1:1) reaction product.

EXAMPLE 20

In an autoclave of acid-proof steel fitted with a stirrer and heating or cooling bath there were charged 62 grams (1 mole) of ethylene glycol and 0.3 g (0.5%) zinc perchlorate as catalyst. In addition, a control run was made without catalyst.

In each run, the autoclave was closed following addition of the ethylene glycol and catalyst, and the air was expelled by repeated evacuations and flushings with nitrogen gas. The temperature was then brought to 130° to 140° C, and liquid ethylene oxide introduced at such a rate that the pressure did not exceed 700 kPa (7 kp/cm²). The addition of ethylene oxide was discontinued when 276 grams (6.9 moles) had been introduced. The temperature was then held at 130° to 140° C until the pressure became constant, indicating that all of the ethylene oxide had reacted. The autoclave was then cooled, opened, and its contents analyzed.

The reaction required a total of 20 hours. The reaction velocity decreased during the course of the reaction.

Upon dilution with distilled water, the reaction product gave a practically neutral reaction (pH 5.7). The composition was determined by gas chromatography using a Perkin-Elmer Gas Chromotograph Model 900 with 1 m column of ⅛ inch aluminum tube filled with Chromosorb 103, and at a programmed rate of increase of temperature of 12° C/min., from 50° to 270° C.

The reaction product had a hydroxyl number of 5.70 moles/g based on the charge of 5.5 moles/g.

In the run without the catalyst, only an insignificant reaction was noted.

EXAMPLE 21

In an autoclave of acid-proof steel, fitted with a stirrer and heating or cooling bath, there were charged 269 grams (1 mole) of oleyl amine and 0.13 g (0.5%) zinc perchlorate. In addition, a control run was made without catalyst.

The autoclave was closed following addition of the oleyl amine and catalyst, and the air was expelled by repeated evacuations and flushings with nitrogen gas. The temperature was then brought to 120° C and liquid ethylene oxide introduced at such a rate that the pressure did not exceed 700 kPa (7 kp/cm²). The addition of ethylene oxide was discontinued when 308 grams (7 moles) had been introduced. The reaction started at once. The temperature was then held at 120° C for 5 hours, when the pressure became constant, indicating that all of the ethylene oxide had reacted. The reaction velocity decreased towards the end of the reaction. The autoclave was then cooled, opened, and its contents analyzed.

The reaction began at once and was complete after five hours.

The reaction product was titrated and found to contain 1.78 moles/g of nitrogen, calculated on the charge of 1.76 moles/g.

The run without a catalyst had a long induction period before reaction began, and when reaction began, it became quite difficult to control. In contast, using the catalyst of the invention, no induction period was observed, and the reaction proceeded rapidly, with no complications.

EXAMPLE 22

In an autoclave of acid-proof steel fitted with a stirrer and heating or cooling bath there were charged 46 grams (one mole) of ethanol and 0.7 g (1.5%) magnesium perchlorate.

The autoclave was closed following addition of the ethanol and catalyst, and the air was expelled by repeated evacuations and flushings with nitrogen gas. The temperature was then brought to 120° C, and liquid propylene oxide-1,2 introduced at such a rate that the pressure did not exceed 700 kPa (7 kp/cm²). The addition of ethylene oxide was discontinued when 58 grams (1 mole) had been introduced. The temperature was then held at 120° C for 9.5 hours, when the pressure became constant, indicating that all of the propylene oxide had reacted. The autoclave was then cooled, opened, and its contents analyzed.

Upon dilution with distilled water, the reaction product gave a practically neutral reaction (pH 5.7). The composition was determined by gas chromatography using a Perkin-Elmer Gas Chromatograph Model 900 with 1 m column of ⅛ inch aluminum tube filled with Chromosorb 103, and at a programmed rate of increase of temperature of 12° C/min., from 50°to 270° C. The analytical results are reported in Table V below as apparent percent, since all reaction products were not determined.

TABLE V

| | Composition Apparent Percent[1] | | |
|---|---|---|---|
| None | One | Two | Three |
| 13 | 57 | 21 | 7 |

[1] Number of moles of ethylene oxide reacted per mole of isopropyl alcohol.

EXAMPLE 23

In an autoclave of acid-proof steel, fitted with a stirrer and heating or cooling bath, there were charged 186 grams (one mole) of lauryl alcohol and 2.7 g (1.5%) magnesium perchlorate.

The autoclave was closed following addition of the lauryl alcohol and catalyst, and the air was expelled by repeated evacuations and flushings with nitrogen gas. The temperature was then brought to 125° C and liquid butylene oxide-1,2 introduced at such a rate that the pressure did not exceed 700 kPa (7 kp/cm$^2$). The addition of butylene oxide was discontinued when 72 grams (1 mole) had been introduced. The temperature was then held at 125° C for 5 hours, until the pressure became constant, indicating that all of the butylene oxide had reacted. The autoclave was then cooled, opened, and its contents analyzed.

Upon dilution with distilled water, the reaction product gave a practically neutral reaction (pH 5.7). The composition was determined by gas chromatography using a Perkin-Elmer Gas Chromatograph Model 900 with 1 m column of ⅛ inch aluminum tube filled with Chromosorb 103, and at a programmed rate of increase of temperature of 12° C/min., from 50° to 270° C. The analytical results are reported in Table VI below as apparent percentage since all reaction products were not determined.

TABLE VI

| | Composition Apparent Percent[1] | | |
|---|---|---|---|
| None | One | Two | Three |
| 31 | 53 | 13 | — |

[1] Number of moles of ethylene oxide reacted per mole of isopropyl alcohol.

EXAMPLE 24

In a 500 ml glass reaction flask provided with reflux condenser, thermometer, stirrer, and separating funnel, there were charged 186 grams (1 mole) of dodecanol. The dodecanol was melted by heating the reaction vessel slowly from beneath, using an oil bath to 40° C, and in the melt there was then dissolved 3.9 grams zinc perchlorate (2% by weight of the dodecanol). The addition of epichlorohydrin (92 g 1 mole) was begun dropwise from the separating funnel with stirring. Addition of epichlorohydrin was complete after 1 hour. The reaction temperature was then brought slowly to 120° C in the course of 3 hours, after which the reaction was discontinued.

The reaction product was subjected to gas chromatographic analysis, and found to contain no unreacted eipichlorohydrin, and only a small amount of unreacted dodecanol. The principal reaction product was dodecyl-2-hydroxy-3-chloropropyl ether (the chloroglyceryl ether of dodecanol, $C_{12}H_{25}OCH_2CH(OH)CH_2Cl$).

Having regard to the foregoing disclosure, the following is claimed as the inventive patentable embodiments thereof:

1. In the process for the addition reaction of organic compounds having an active hydrogen selected from the group consisting of monohydric alcohols, polyols and amines with an epoxide, the improvement which comprises carrying out the reaction at a temperature within the range from about 80 to about 200° C at which the reaction proceeds in the presence of a concentration within the range from about 0.001% to about 10% by weight of the organic compound of an inorganic salt catalyst developing no appreciable acidity or alkalinity in the course of the reaction, accelerating the reaction, and favoring a narrow molecular distribution of adduct species in the reaction product, selected from the group consisting of sodium fluoborate and magnesium, calcium, manganese, nickel and zinc perchlorates.

2. A process according to clim 1, in which the catalyst is zinc perchlorate.

3. A process according to claim 1, in which the catalyst concentration is within the range from about 0.01% to about 1% by weight of the organic compound.

4. A process according to claim 1, in which the catalyst concentration is within the range from about 0.5 to about 5% by weight of the organic compound, and the organic compound has more than seven carbon atoms.

5. A process according to claim 1, in which the reaction temperature is within the range from about 100° to about 150° C.

6. A process according to claim 1 in which the organic compound has from about one to about thirty carbon atoms.

7. A process according to claim 1 in which the monohydric alcohol is an aliphatic alcohol.

8. A process according to claim 1 in which the alcohol is selected from the group consisting of aliphatic, cycloaliphatic and phenyl-substituted aliphatic monohydric alcohols, and halogen-substituted such alcohols.

9. A process according to claim 1 in which the polyol has from two to thirty carbon atoms and from two to six hydroxyl groups.

10. A process according to claim 1 in which the amine is selected from the group consisting of aromatic primary and secondary mono and polyamines.

11. A process according to claim 1 in which the epoxide is selected from the group consisting of aliphatic, cycloaliphatic and phenyl-substituted aliphatic epoxides having from two to about thirty carbon atoms.

12. A process according to claim 11 in which the epoxide is selected from the group consisting of ethylene oxide, propylene oxide, butylene oxide, epichlorohydrin, cyclohexene oxide, cyclopentene oxide, styrene oxide, α-methylstyrene oxide and glycidol.

13. A process according to claim 12 in which the epoxide is ethylene oxide.

* * * * *